United States Patent
Won

(10) Patent No.: US 10,111,629 B2
(45) Date of Patent: Oct. 30, 2018

(54) IMAGING STAND

(71) Applicant: SAMSUNG ELECTRONICS CO., LTD., Suwon-si, Gyeonggi-do (KR)

(72) Inventor: Suk Hee Won, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 410 days.

(21) Appl. No.: 14/564,745

(22) Filed: Dec. 9, 2014

(65) Prior Publication Data

US 2015/0208995 A1   Jul. 30, 2015

(30) Foreign Application Priority Data

Jan. 29, 2014   (KR) .................. 10-2014-0011612

(51) Int. Cl.
*G03B 41/02* (2006.01)
*A61B 6/00* (2006.01)
*A61B 6/04* (2006.01)

(52) U.S. Cl.
CPC .......... *A61B 6/4452* (2013.01); *A61B 6/0407* (2013.01); *A61B 6/4405* (2013.01); *A61B 6/4464* (2013.01)

(58) Field of Classification Search
CPC .... G03B 42/025; G03B 42/045; G03B 42/02; G03B 42/04
See application file for complete search history.

(56) References Cited

U.S. PATENT DOCUMENTS

| | | | | |
|---|---|---|---|---|
| 2,598,529 A * | 5/1952 | Fritz | .................... | G03B 42/025 248/124.2 |
| 5,301,221 A * | 4/1994 | Yakubisin | ............ | G03B 42/025 378/167 |
| 5,944,468 A * | 8/1999 | McBrien | ............. | E04F 21/1805 248/410 |
| 6,434,218 B1 * | 8/2002 | Matsumoto | .............. | G21K 1/04 378/154 |
| 8,065,758 B1 * | 11/2011 | Mendez | ............... | A47K 5/1202 4/654 |

FOREIGN PATENT DOCUMENTS

| | | |
|---|---|---|
| EP | 1 876 953 | 11/2005 |
| EP | 2 609 859 | 12/2012 |
| KR | 20-2011-0006027 | 6/2011 |
| KR | 10-2011-0084577 | 7/2011 |

* cited by examiner

*Primary Examiner* — Hoon Song
(74) *Attorney, Agent, or Firm* — Staas & Halsey LLP

(57) ABSTRACT

An imaging stand includes a frame, a plate provided to be movable along the frame, and a fixing device provided in a rear surface of the plate and configured to fix the plate in the frame. The fixing device includes a first pressing part in which a first hole through which the frame penetrates is formed, and a second pressing part that faces the first pressing part, is formed such that a minimum distance to the first pressing part becomes longer from one side to the other side, and in which a second hole through which the frame penetrates is formed.

14 Claims, 12 Drawing Sheets

IMAGING STAND

CROSS-REFERENCE TO RELATED APPLICATIONS

This application claims the benefit of Korean Patent Application No. 10-2014-0011612, filed on Jan. 29, 2014 in the Korean Intellectual Property Office, the disclosure of which is incorporated herein by reference.

BACKGROUND

1. Field

Embodiments of the present disclosure relate to an imaging stand for an X-ray imaging apparatus.

2. Description of the Related Art

An X-ray imaging apparatus is an apparatus for obtaining an image of an inside of a subject using X-rays. The X-ray imaging apparatus radiates X-rays onto the subject, detects X-rays transmitted through the subject, and is able to image the inside of the subject in a noninvasive manner. A medical X-ray imaging apparatus may be used to diagnose injuries, diseases, and the like inside the subject that cannot be identified externally.

The X-ray imaging apparatus includes an X-ray source configured to generate and radiate X-rays onto the subject and a detector configured to detect X-rays transmitted through the subject. The X-ray source may be movable such that various parts of the subject can be imaged. The detector may be mounted on an imaging table or an imaging stand.

A grid may be provided in front of the detector. When the grid is provided, scattering light of X-rays is blocked, thereby preventing an image of an affected part of the subject from being blurred.

SUMMARY

According to an embodiment of the present disclosure, it is possible to provide an imaging stand capable with which a detector and a grid can be placed at a desired height.

According to an aspect of the present disclosure, there is provided an imaging stand. The imaging stand includes a frame, a plate provided to be movable along the frame, and a fixing device provided in a rear surface of the plate and configured to fix the plate in the frame, wherein the fixing device includes a first pressing part in which a first hole through which the frame penetrates is formed, and a second pressing part that faces the first pressing part, is formed such that a minimum distance to the first pressing part becomes longer from one side to the other side, and in which a second hole through which the frame penetrates is formed.

When a distance between the other side of the first pressing part and the other side of the second pressing part becomes shorter due to external force, a fixing state of the fixing device may be released, and thereby the plate may move along the frame.

When the external force applied to the other side of the first pressing part and the other side of the second pressing part is released, an inner side surface of the fixing device forming the first hole or the second hole may press the frame, thereby fixing the fixing device in the frame.

A plurality of fixing grooves into which an inner side surface of the fixing device forming the first hole or the second hole is inserted may be formed in an outer circumferential surface of the frame.

The plurality of fixing grooves may extend in a direction orthogonal to an extending direction of the frame.

A fixing holder capable of supporting an X-ray detecting unit may be provided in a lower end of the plate, and a moving holder configured to fix an upper side of the X-ray detecting unit and be movable along the frame may be provided in an upper side of the plate.

The moving holder may move along the frame due to the force of gravity.

The fixing holder may be formed by bending the lower end of the plate.

The plate may include a first plate in which a detector is located and a second plate in which a grid is located.

The fixing device may include a first fixing device provided in a rear surface of the first plate and a second fixing device provided in a rear surface of the second plate.

A first fixing holder configured to support the detector may be provided in a lower end of the first plate, and a first moving holder configured to fix an upper side of the detector and be movable along the frame may be provided in an upper side of the first plate.

A second fixing holder configured to support the grid may be provided in a lower end of the second plate, and a second moving holder configured to fix an upper side of the grid and be movable along the frame may be provided in an upper side of the second plate.

Either the first plate or the second plate may be formed by cutting a part of the other plate.

A center line extending in a length direction of the frame may be provided in the frame.

The center line may be a groove extending in a length direction of the frame.

According to another aspect of the present disclosure, there is provided an imaging stand. The imaging stand includes a frame in which a center line extending in a length direction is provided, a plate in which an X-ray detecting unit is located and that is movably mounted along the frame, and a fixing device configured to connect the plate and the frame, wherein the fixing device includes a connecting part mounted on the plate, and a first pressing part and a second pressing part which face and extend from the connecting part such that a minimum distance becomes longer from one side to the other side.

The plate may include a first plate configured to support a detector and a second plate configured to support a grid and be separately movable from the first plate.

The frame may penetrate a first hole formed in the first pressing part and a second hole formed in the second pressing part.

While external force is applied such that the other side of the first pressing part and the other side of the second pressing part become closer, the fixing device may move in a length direction of the frame.

When the external force applied to the other side of the first pressing part and the other side of the second pressing part is released, the first pressing part and the second pressing part may be restored to a state before the external force is applied, and an inner wall of the first pressing part forming the first hole and an inner wall of the second pressing part forming the second hole may press the frame, thereby fixing the fixing device in the frame.

Additional aspects and/or advantages will be set forth in part in the description which follows and, in part, will be apparent from the description, or may be learned by practice of the disclosure.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Hereinafter, an imaging stand according to an embodiment of the present disclosure will be described in detail with reference to the drawings.

Figure 1:
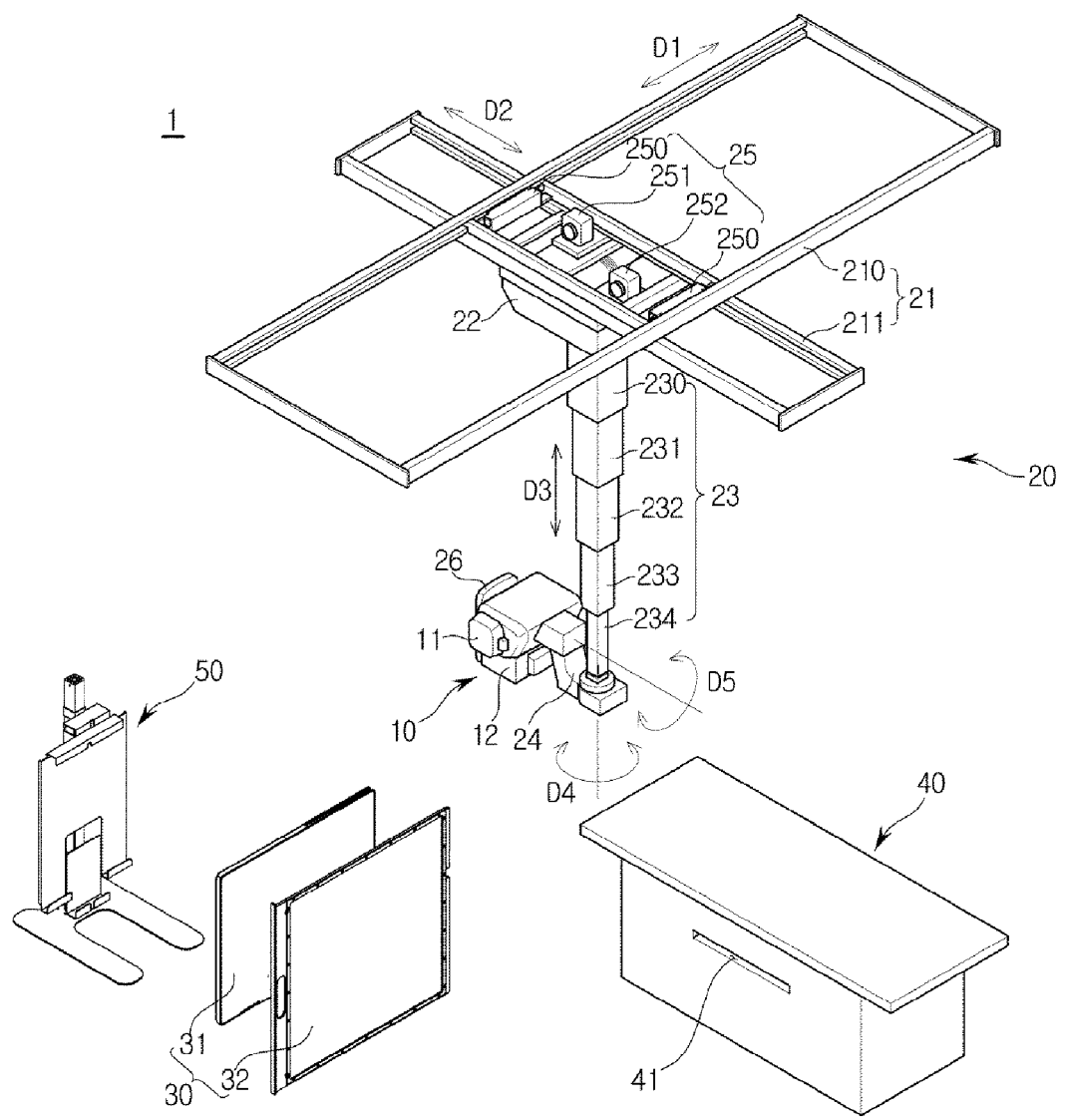
FIG. 1 is a diagram illustrating an X-ray imaging apparatus according to an embodiment of the present disclosure.

FIG. 1 is a diagram illustrating an X-ray imaging apparatus according to an embodiment of the present disclosure.

As illustrated in FIG. 1, an X-ray imaging apparatus 1 according to the embodiment of the present disclosure may include an X-ray generating unit 10 and an X-ray detecting unit 30.

The X-ray generating unit 10 generates X-rays and radiates the X-rays onto a subject. The X-ray generating unit 10 generates the X-rays using power supplied from a power supply unit (not illustrated). X-ray energy may be controlled by a tube voltage, and an intensity or a dose of X-rays may be controlled by a tube current and an X-ray exposure time.

The X-ray detecting unit 30 detects X-rays transmitted through the subject. The X-ray detecting unit 30 may obtain X-ray data by converting the detected X-rays into an electrical signal.

The X-ray imaging apparatus 1 may include a moving unit 20 for moving the X-ray generating unit 10. The moving unit 20 may include a guide rail 21, a moving carriage 22, and a column 23.

The guide rail 21 includes a first guide rail 210 and a second guide rail 211. The first guide rail 210 and the second guide rail 211 may be installed to form a predetermined angle. For example, the first guide rail 210 and the second guide rail 211 may extend orthogonally. A direction in which the first guide rail 210 extends is defined as a first direction D1. A direction in which the second guide rail 211 extends is defined as a second direction D2. The first direction D1 and the second direction D2 may be orthogonal to each other.

The first guide rail 210 may be installed in a ceiling of a laboratory in which the X-ray imaging apparatus 1 is disposed. The second guide rail 211 may be located below the first guide rail 210. The second guide rail 211 may be slidably mounted on the first guide rail 210. For example, a roller that is movable along the first guide rail 210 is installed in the first guide rail 210, and the second guide rail 211 is connected to the roller and is movable along the first guide rail 210.

The moving carriage 22 may be disposed below the second guide rail 211. The moving carriage 22 may be provided to be movable along the second guide rail 211. A roller that is movable along the second guide rail 211 is installed in the moving carriage 22. The moving carriage 22 is movable in the first direction D1 together with the second guide rail 211, and is also movable in the second direction D2 along the second guide rail 211.

The column 23 may be located below the moving carriage 22. The column 23 may include a plurality of column units 230, 231, 232, 233, and 234. The plurality of column units 230, 231, 232, 233, and 234 may be telescopically connected. A length of the column 23 may increase or decrease in a vertical direction of the laboratory while being fixed in the moving carriage 22. A direction in which the length of the column 23 increases or decreases may be defined as a third direction D3. The third direction D3 may be orthogonal to both the first direction D1 and the second direction D2.

The X-ray generating unit 10 is a unit for radiating X-rays onto the subject. The X-ray generating unit 10 may include an X-ray source 11 and a collimator 12. The X-ray source 11 generates X-rays. The collimator 12 guides the X-rays generated from the X-ray source 11 toward the subject.

A rotary joint 24 may be disposed between the X-ray generating unit 10 and the column 23. The rotary joint 24 enables the X-ray generating unit 10 to be combined with the column 23 and is able to support a load applied to the X-ray generating unit 10.

The X-ray generating unit 10 is able to rotate around the rotary joint 24. The X-ray generating unit 10 is able to rotate in a fourth direction D4 or a fifth direction D5 by the rotary joint 24. The fourth direction D4 may be a direction of rotating around an axis parallel to the third direction D3. The fifth direction D5 may be a direction of rotating around an axis parallel to the first direction D1 or the second direction D2.

The X-ray generating unit 10 is connected to the rotary joint 24 and is able to rotate in the fourth direction D4 or the fifth direction D5. Also, the X-ray generating unit 10 is connected to the column 23 by the rotary joint 24, and is able to linearly move in the first direction D1, the second direction D2, or the third direction D3.

A driving unit 25 may be provided in order to move the X-ray generating unit 10 in the first to fifth directions D1 to D5. The driving unit 25 may be a motor that is electrically driven.

The driving unit 25 may be provided to correspond to the first to fifth directions D1 to D5. For example, the driving unit 25 may include a first driving unit 250 configured to move the second guide rail 211 in the first direction D1 and second driving units 251 and 252 configured to move the moving carriage 22 in the second direction D2. The first driving unit 250 may be disposed in the vicinity of the first guide rail 210, and the second driving units 251 and 252 may be disposed in the vicinity of the second guide rail 211.

The driving unit 25 may include a third driving unit (not illustrated) configured to increase or decrease the length of the column 23 in the third direction D3, a fourth driving unit (not illustrated) configured to rotate the X-ray generating unit 10 in the fourth direction D4, and a fifth driving unit (not illustrated) configured to rotatably move the X-ray generating unit 10 in the fifth direction D5. The third driving unit may be disposed inside the moving carriage 22. The fourth driving unit and the fifth driving unit may be disposed in the vicinity of the rotary joint 24.

A manipulating unit 26 configured to input various pieces of information on X-ray imaging and manipulate respective devices may be provided at one side of the X-ray generating unit 10.

The X-ray imaging apparatus 1 may further include an imaging table 40 or an imaging stand 50 on which the X-ray detecting unit 30 is mounted. When the subject is imaged while lying on the imaging table 40, the X-ray detecting unit 30 may be inserted into an accommodating part 41 provided in the imaging table 40. When the subject is imaged while standing, the X-ray detecting unit 30 may be mounted on the imaging stand 50.

The X-ray detecting unit 30 may include a detector 31 and a grid 32. The detector 31 may detect X-rays passing through the subject and convert the X-rays into an electrical signal. X-ray data on the subject may be obtained by the detector 31. The grid 32 is located in front of the detector 31, thereby blocking scattering light of X-rays generated from the X-ray source 11. The scattering light of X-rays is blocked by the grid 32, and thereby accurate X-ray data on the subject is obtained.

Hereinafter, a structure of the imaging stand 50 on which the X-ray detecting unit 30 is mounted will be described in detail with reference to the drawings.

Figure 2A:
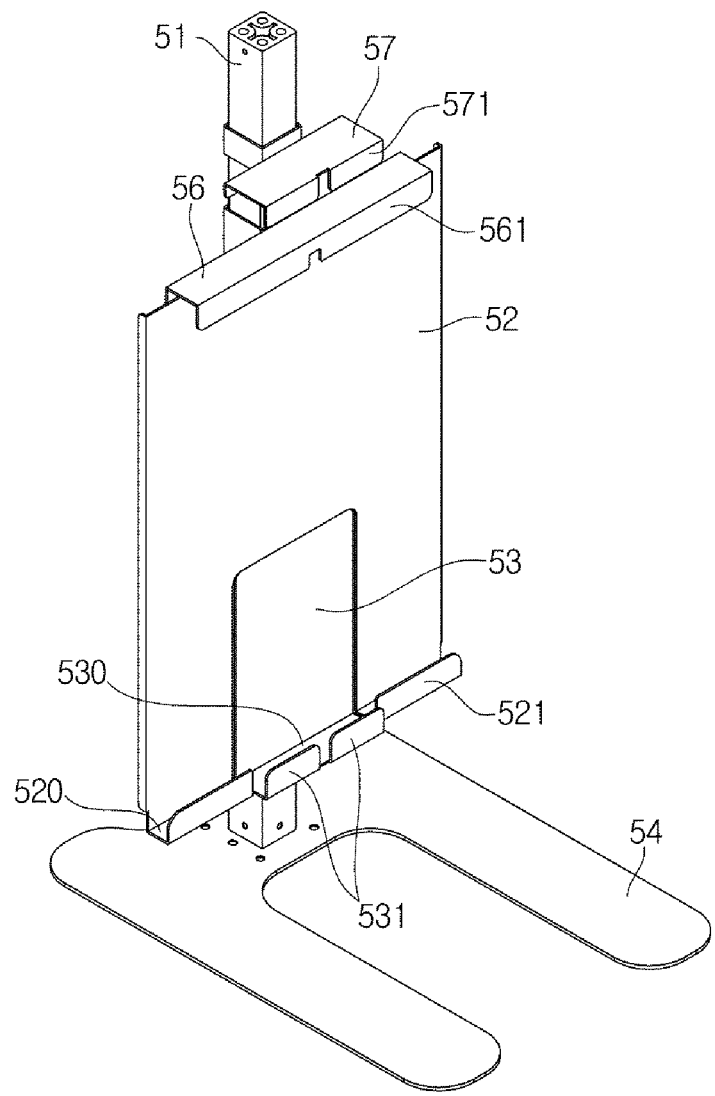
FIG. 2A is a diagram illustrating an appearance seen from a front of an imaging stand according to an embodiment of the present disclosure.
Figure 2B:
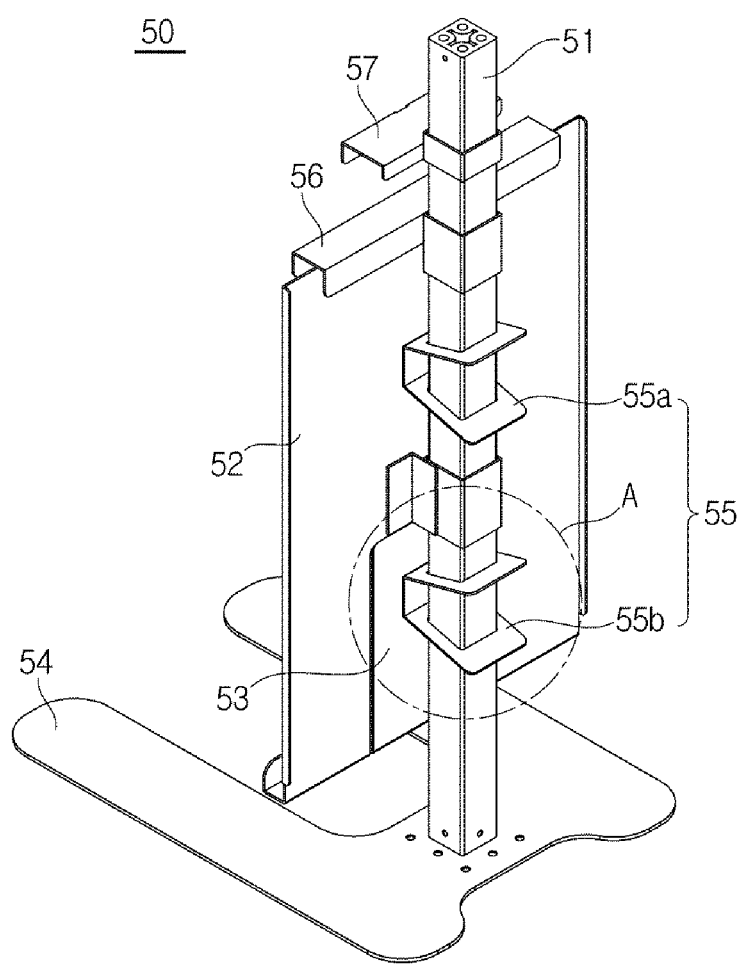
FIG. 2B is a diagram illustrating an appearance seen from a rear of the imaging stand according to the embodiment of the present disclosure.
Figure 3A:
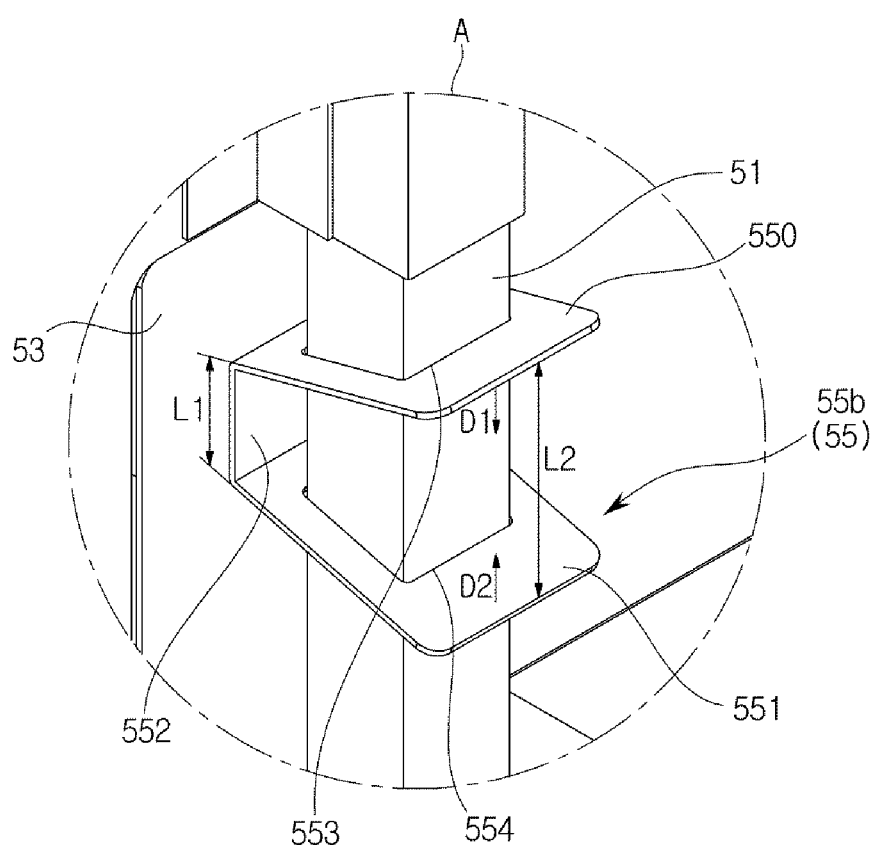
FIGS. 3A and 3B are partial perspective views illustrating a part A in FIG. 2B.
Figure 3B:
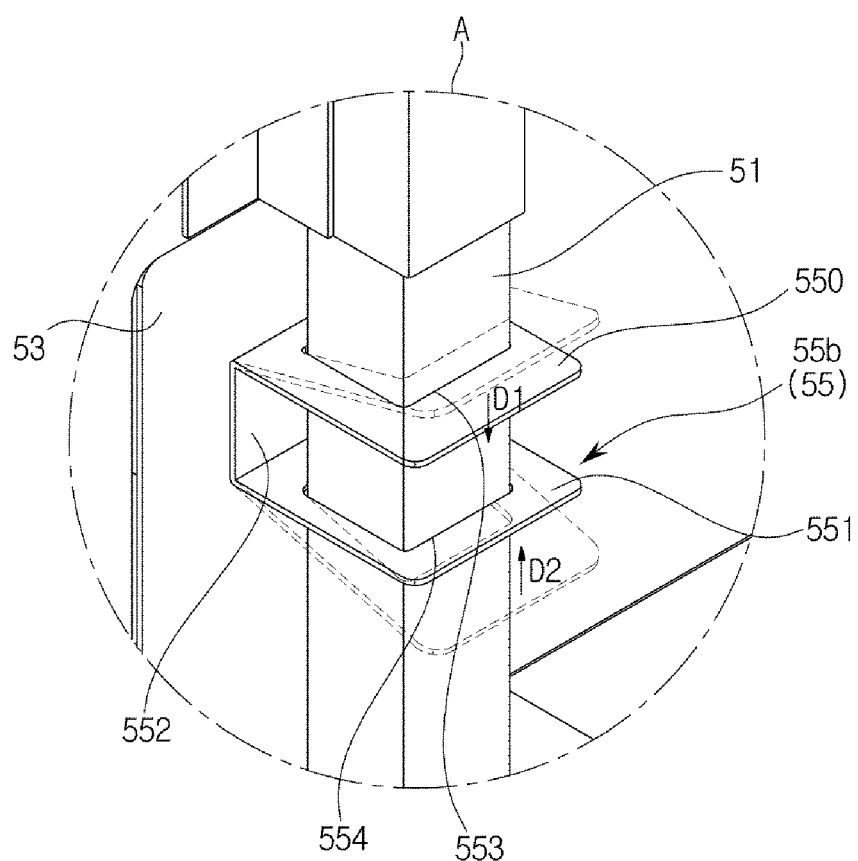

FIG. 2A is a diagram illustrating an appearance seen from a front of an imaging stand according to an embodiment of the present disclosure. FIG. 2B is a diagram illustrating an appearance seen from a rear of the imaging stand according to the embodiment of the present disclosure. FIGS. 3A and 3B are partial perspective views illustrating a part A in FIG. 2B.

As illustrated in FIGS. 2A to 3B, the imaging stand 50 according to the embodiment of the present disclosure may include a frame 51, a first plate 52, a second plate 53, and a base 54. The frame 51 may stand on and be fixed in the base 54. Hereinafter, an extending direction of the frame 51 may be defined as a vertical direction. The base 54 may be arranged on a floor surface. The first plate 52 and the second plate 53 may be slidably provided along the frame 51 in the vertical direction.

The detector 31 may be located in the first plate 52. First holders 56 and 520 may be provided in at least one side of the first support plate 52. The detector 31 is located in front of the first plate 52 and may be fixed by the first holders 56 and 520.

The first holders 56 and 520 include the first moving holder 56 and the first fixing holder 520. The first moving holder 56 may be separately provided from the first plate 52. The first moving holder 56 is located above the first plate 52 and is able to fix an upper part of the detector 31. The first moving holder 56 is mounted on the frame 51 and may be provided to freely move along the frame 51 in the vertical direction. The first moving holder 56 may be provided to move down due to the force of gravity.

When the detector 31 is located in front of the first plate 52 and external force is released, the first moving holder 56 is lowered by the force of gravity and may interfere with the upper part of the detector 31. The first moving holder 56 may be formed to be bent such that a space into which an upper part of the detector 31 is inserted is provided. A part of the first moving holder 56 is located in front of the detector 31 and may be bent so as to fix the detector 31. A part of the first moving holder 56 that extends so as to interfere with an upper front of the detector 31 may be called a first fixing unit 561.

The first fixing holder 520 may be provided in a lower end of the first plate 52. The first fixing holder 520 may support the detector 31. The first fixing holder 520 may be formed by bending a part of the first plate 52. The first fixing holder 520 may be formed to be bent such that a space into which a lower end of the detector 31 is inserted is provided. A part of the first fixing holder 520 is located in front of the detector 31 and may be bent so as to fix the detector 31. A part of the first fixing holder 520 that extends so as to interfere with a lower front of the detector 31 may be called a second fixing unit 521.

When the detector 31 is located in the first plate 52, the detector 31 may be fixed by the first moving holder 56 and the first fixing holder 520. The upper part of the detector 31 may be fixed by the first moving holder 56, and a lower part of the detector 31 may be fixed by the first fixing holder 520. The first moving holder 56 is separately provided from the first plate 52 and is movable in the vertical direction such that the detector 31 of various sizes is located and fixed in the first plate 52.

The second plate 53 may be provided by cutting a part of the first plate 52. The second plate 53 may be slidably provided along the frame 51 in the vertical direction, separately from the first plate 52. The grid 32 is located in front of the second plate 53 and may be fixed by second holders 57 and 530.

While the second plate 53 is provided by cutting a part of the first plate 52 in the above description, the first plate 52 may be provided by cutting a part of the second plate 53. Hereinafter, description will be provided assuming that the second plate 53 is provided by cutting a part of the first plate 52.

The second holders 57 and 530 include the second moving holder 57 and the second fixing holder 530. The second moving holder 57 may be separately provided from the second plate 53. The second moving holder 57 may be located above the first plate 52. For example, the second moving holder 57 may be located above the first moving holder 56.

The second moving holder 57 is mounted on the frame 51 and is provided to freely move along the frame 51 in the vertical direction. The second moving holder 57 may move down along the frame 51 due to the force of gravity. When the grid 32 is located in the second plate 53 and the external force is released, the second moving holder 57 is lowered due to the force of gravity and may interfere with an upper part of the grid 32.

The second moving holder 57 is bent and thereby a space into which an upper part of the grid 32 is inserted may be provided. A part of the second moving holder 57 is located in front of the grid 32 and may be bent so as to fix the grid 32. A part of the second moving holder 57 that extends so as to interfere with an upper front of the grid 32 may be called a third fixing unit 571.

The second fixing holder 530 may be provided in a lower end of the second plate 53. The second fixing holder 530 may support the grid 32. The second fixing holder 530 may be formed by bending a part of the second plate 53. The second fixing holder 530 may be formed to be bent such that a space into which a lower part of the grid 32 is inserted is provided. A part of the second fixing holder 530 is located in front of the grid 32 and may be bent so as to fix the grid 32. A part of the second fixing holder 530 that extends so as to interfere with a lower front of the grid 32 may be called a fourth fixing unit 531.

When the grid 32 is located in front of the detector 31, the grid 32 may be fixed by the second moving holder 57 and the second fixing holder 530. The upper part of the grid 32 may be fixed by the second moving holder 57, and the lower part of the grid 32 may be fixed by the second fixing holder 530. The second moving holder 57 is separately provided from the second plate 53 and is movable in the vertical direction such that the grid 32 of various sizes is located in front of the detector 31 and fixed.

Meanwhile, since the grid 32 is located in front of the detector 31, the second moving holder 57 and the second fixing holder 530 may be formed to protrude forward more than the first moving holder 56 and the first fixing holder 520.

The first plate 52 and the second plate 53 may be fixed at a specific height of the frame 51 by a fixing device 55. The fixing device 55 is provided in a rear surface of the first plate 52 or the second plate 53, and may be mounted on the frame 51.

The fixing device 55 includes a first fixing device 55a and a second fixing device 55b. The first fixing device 55a may be provided in the rear surface of the first plate 52. The second fixing device 55b may be provided in the rear surface of the second plate 53.

Hereinafter, a structure of the second fixing device 55b will be described. Description of the structure of the second fixing device 55b may be similarly applied to the first fixing device 55a.

The second fixing device 55b includes a first pressing part 550, a second pressing part 551, and a connecting part 552. The first pressing part 550 and the second pressing part 551 may be connected by the connecting part 552. The first pressing part 550 extends from one side of the connecting part 552. The second pressing part 551 may extend from the other side facing the one side of the connecting part 552. The first pressing part 550 and the second pressing part 551 may be provided so as to face each other. The connecting part 552 may be mounted on the rear surface of the second plate 53.

In the first pressing part 550, a first hole 553 through which the frame 51 penetrates may be formed. In the second pressing part 551, a second hole 554 through which the frame 51 penetrates may be formed. By allowing the frame 51 to penetrate through the first hole 553 and the second hole 554, the second fixing device 55b may be mounted on the frame 51. The first hole 553 and the second hole 554 may be formed to correspond to a shape of an outer circumferential surface of the frame 51. The first hole 553 and the second hole 554 may be formed to be slightly larger than a cross section of the frame 51.

The first pressing part 550 may extend such that a minimum distance from the second pressing part 551 increases from one side to the other side of the first pressing part 550. Similarly, the second pressing part 551 may extend such that a distance from the first pressing part 550 increases from one side to the other side of the second pressing part 551.

In the first pressing part 550 and the second pressing part 551, a distance L2 between the other side of the first pressing part 550 and the other side of the second pressing part 551 is longer than a distance L1 between the one side of the first pressing part 550 and the one side of the second pressing part 551. The distance L1 between the one side of the first pressing part 550 and the one side of the second pressing part 551 may be a length of the connecting part 552 in the vertical direction.

While there is no external force, the second fixing device 55b may be fixed in the frame 51. While the other side of the first pressing part 550 is pressed downward (D1) and the other side of the second pressing part 551 is pressed upward (D2), an operator may move the second fixing device 55b upward or downward with respect to the frame 51. At this time, the distance L2 between the other side of the first pressing part 550 and the other side of the second pressing part 551 may be the same as or similar to the distance L1 between the one side of the first pressing part 550 and the one side of the second pressing part 551.

When the external force applied to the second fixing device 55b is released, the distance between the first pressing part 550 and the second pressing part 551 may be restored to a state before the external force is applied due to elasticity. In other words, the distance L2 between the other side of the first pressing part 550 and the other side of the second pressing part 551 may become longer than the distance L1 between the one side of the first pressing part 550 and the one side of the second pressing part 551. While the second fixing device 55b is restored to a state before pressing, an inner wall of the second fixing device 55b forming the first hole 553 and the second hole 554 presses the frame 51. Due to restoring force of the second fixing device 55b, the second fixing device 55b may be fixed in the frame 51.

As described above, the second plate 53 on which the grid 32 is mounted may be fixed in the frame 51 due to the restoring force of the second fixing device 55b. The operator applies the external force to the second fixing device 55b, releases a fixing state of the second fixing device 55b, and may adjust a height of the second plate 53. The operator may move the second plate 53 in the extending direction of the frame 51 while the external force is applied to the second fixing device 55b. When the second plate 53 is located at a desired height, the external force applied to the second fixing device 55b is released, thereby fixing the second plate 53 at a desired height.

Similarly, the first plate 52 on which the detector 31 is mounted may be fixed in the frame 51 by the first fixing device 55a. The operator applies the external force to the first fixing device 55a, releases a fixing state of the second fixing device 55b, and may adjust a height of the first plate 52. The operator may move the first plate 52 in the extending direction of the frame 51 while the external force is applied to the first fixing device 55a. When the first plate 52 is located at a desired height, the external force applied to the first fixing device 55 a is released, thereby fixing the first plate 52 at a desired height.

Figure 4:
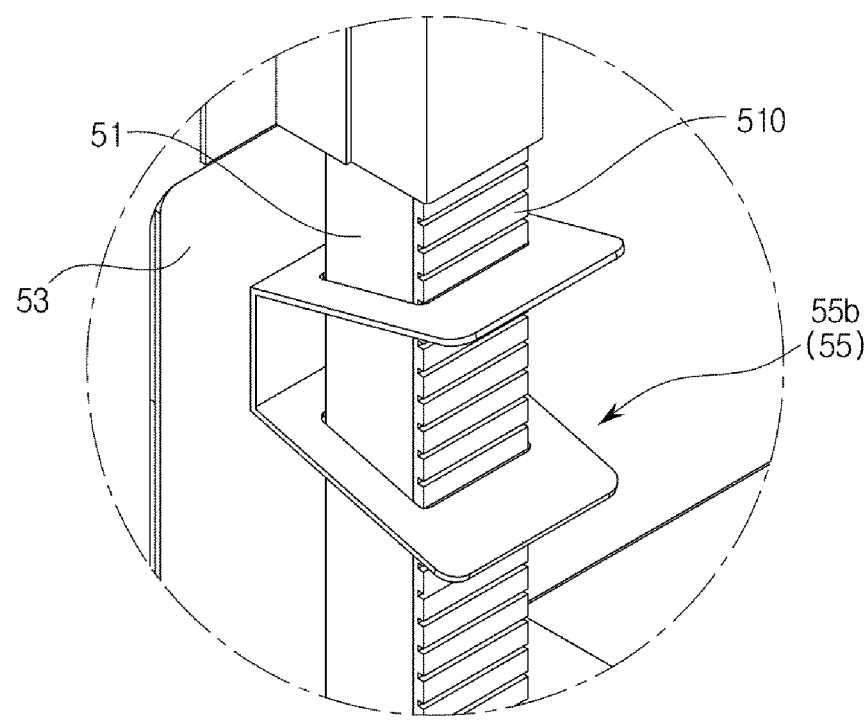
FIG. 4 is a diagram illustrating a frame according to an embodiment of the present disclosure.
Figure 5A:
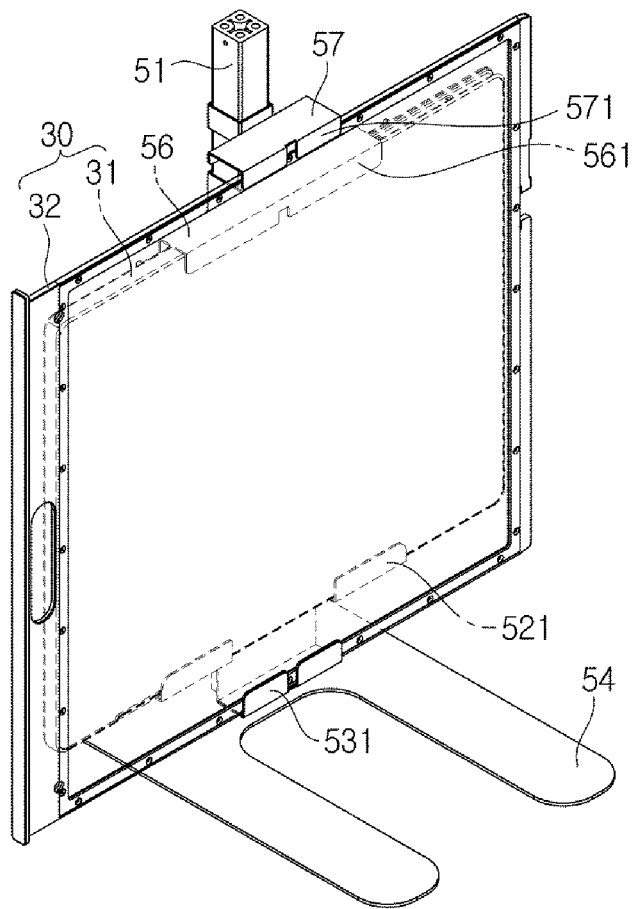
FIGS. 5A and 5B are perspective views illustrating an appearance in which a detector and a grid are mounted on the imaging stand according to the embodiment of the present disclosure.
Figure 5B:
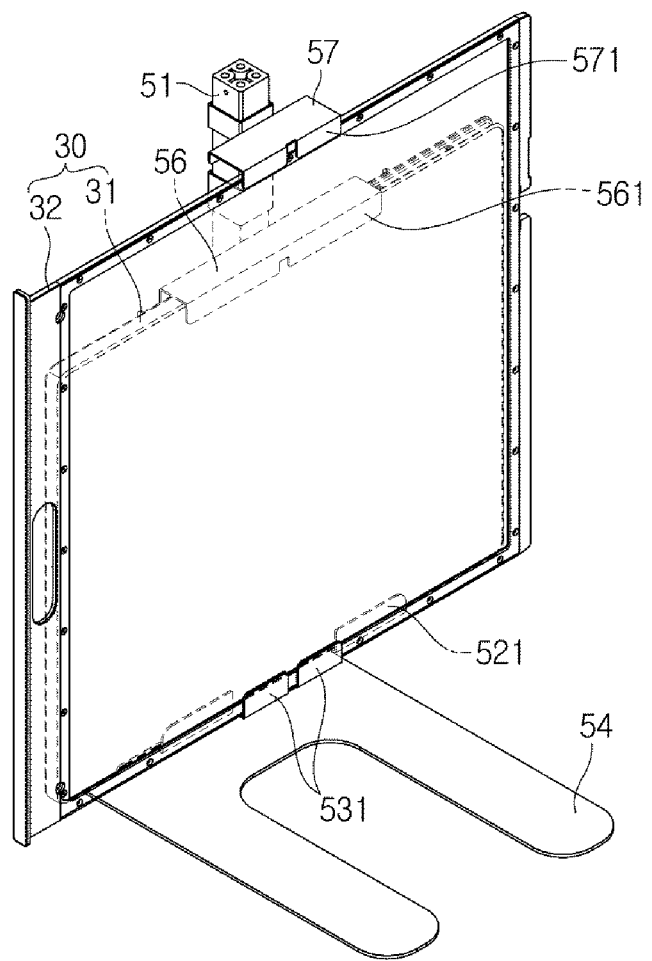
Figure 6A:
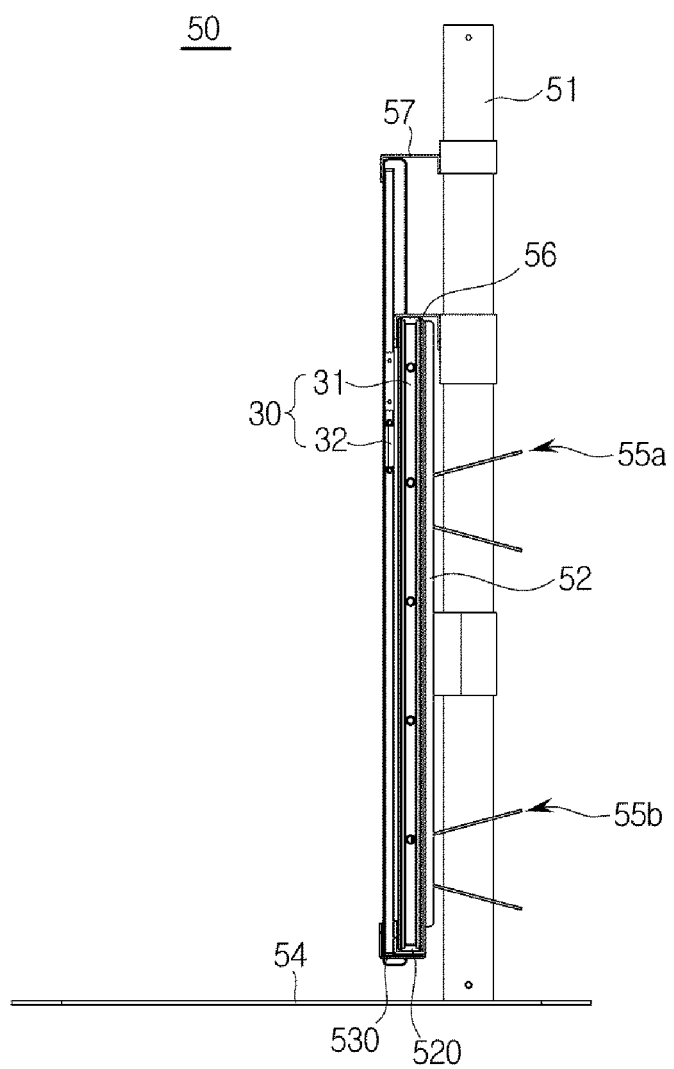
FIGS. 6A and 6B are side views illustrating an appearance in which a detector and a grid are mounted on the imaging stand according to the embodiment of the present disclosure.
Figure 6B:
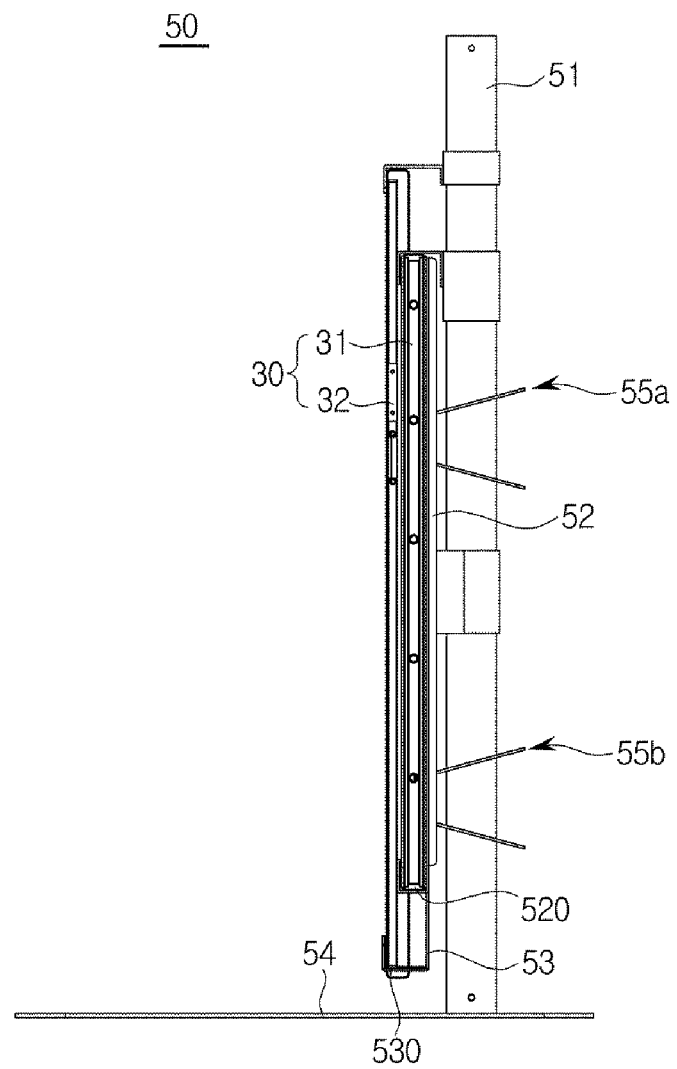

FIG. 4 is a diagram illustrating a frame according to an embodiment of the present disclosure. FIGS. 5A and 5B are perspective views illustrating an appearance in which a detector and a grid are mounted on the imaging stand according to the embodiment of the present disclosure. FIGS. 6A and 6B are side views illustrating an appearance in which a detector and a grid are mounted on the imaging stand according to the embodiment of the present disclosure.

As illustrated in FIGS. 4 to 6B, a fixing groove 510 may be formed in the outer circumferential surface of the frame 51 according to the embodiment of the present disclosure. The fixing groove 510 may extend in a direction orthogonal to the extending direction of the frame 51. The fixing groove 510 may extend in a horizontal direction. In the outer circumferential surface of the frame 51, a plurality of fixing grooves 510 may be separately formed at predetermined intervals. The inner wall forming the first hole 553 or the second hole 554 of the fixing device 55 may be inserted into the fixing groove 510. Accordingly, the fixing device 55 may be fixed so as not to move along the frame 51 in the vertical direction.

The operator presses the first fixing device 55a, makes the first plate 52 to be movable along the frame 51 in the vertical direction, and then may move the first plate 52 along the frame 51 in the vertical direction to be located at a desired height. When the first plate 52 is located at a predetermined height, the operator may release the external force applied to the first fixing device 55a. When the external force applied to the first fixing device 55a is released, the inner wall of the first fixing device 55a forming the first hole or the second hole may be inserted into the fixing groove 510. When the inner wall of the first fixing device 55a is inserted into the fixing groove 510, the first fixing device 55a may be fixed in the frame 51. Accordingly, the first plate 52 may be fixed at a predetermined height.

The operator presses the second fixing device 55b, allows the second plate 53 to move along the frame 51 in the vertical direction, and then may move the second plate 53 along the frame 51 in the vertical direction to be located at a desired height. When the second plate 53 is located at a predetermined height, the operator may release the external force applied to the second fixing device 55b. When the external force applied to the second fixing device 55b is released, the inner wall of the second fixing device 55b forming the first hole 553 or the second hole 554 may be inserted into the fixing groove 510. When the inner wall of the second fixing device 55b is inserted into the fixing groove 510, the second fixing device 55b may be fixed in the frame 51. Accordingly, the second plate 53 may be fixed at a predetermined height.

A height of the second fixing unit 521 provided in the lower end of the first plate 52 may be different from a height of the fourth fixing unit 531 provided in the lower end of the second plate 53. The detector 31 may be arranged in the second fixing unit 521. The grid 32 may be arranged in the fourth fixing unit 531. The height of the second fixing unit 521 and the height of the fourth fixing unit 531 are provided so as to be differently adjusted. Accordingly, the detector 31 or the grid 32 having various sizes and shapes may be mounted on the imaging stand 50.

While the first plate 52 is fixed in the frame 51 by the first fixing device 55a and the second plate 53 is fixed in the frame 51 by the second fixing device 55b in the above description, a method of fixing the first plate 52 or the second plate 53 in the frame 51 is not limited thereto. For example, a fixing shaft in which a screw thread is formed in an outer circumferential surface is provided in a back surface of the first plate 52 or the second plate 53, fixing holes separated a predetermined distance in a length direction of the frame 51 are provided in the frame 51, and the first plate 52 or the second plate 53 may be fixed in the frame 51 by inserting the fixing shaft into the fixing hole. In an end of the fixing shaft penetrating through the fixing hole, a fixing member in which a screw thread corresponding to the screw thread formed in the outer circumferential surface of the fixing shaft is formed in an inner circumferential surface is mounted, thereby preventing the fixing shaft from being separated from the fixing hole. As another example, a fixing groove is provided in the first plate 52 or the second plate 53, and a fixing shaft provided to be brought close to the frame 51 by the elastic member may be provided in the fixing hole formed in the frame 51. When the fixing shaft is pressed in a direction opposite to the elastic force of the elastic member, the fixing shaft may be movable in the length direction of the frame 51. When the fixing shaft is placed at a predetermined height of the frame 51, the external force applied to the fixing shaft is released, and the end of the fixing shaft is inserted into the fixing groove of the first plate 52 or the second plate 53, the first plate 52 or the second plate 53 may be fixed in the frame 51.

When the detector 31 is arranged in the first fixing holder 520 of the first plate 52, the first moving holder 56 located above the first plate 52 may fix an upper end of the detector 31. The operator may move the first moving holder 56 up using an upper end of the detector 31 and arrange the detector 31 in the first fixing holder 520. Alternatively, while the operator raises the first moving holder 56 up with one hand, his or her other hand may move the detector 31 to be arranged in the first fixing holder 520. When the detector 31 is arranged in the first fixing holder 520 and then the first moving holder 56 is released, the first moving holder 56 may be lowered to the upper end of the detector 31. Therefore, the detector 31 may be mounted on the first plate 52.

Similarly, when the grid 32 is arranged in the second fixing holder 530 of the second plate 53, the second moving holder 57 located above the second plate 53 may fix an upper end of the grid 32. The operator may move the second moving holder 57 up using the upper end of the grid 32 and arrange the grid 32 in the second fixing holder 530. Alternatively, while the operator raises the second moving holder 57 up with one hand, his or her other hand may move the grid 32 to be arranged in the second fixing holder 530. When the grid 32 is arranged in the second fixing holder 530 and then the second moving holder 57 is released, the second moving holder 57 may be lowered to the upper end of the grid 32. Therefore, the grid 32 may be mounted on the second plate 53.

As described above, in the imaging stand 50 according to the embodiment of the present disclosure, the first plate 52 and the second plate 53 are provided to be separately movable, and the first moving holder 56 fixing an upper part of the detector 31 and the second moving holder 57 fixing an upper part of the grid 32 may be lowered by its own weight.

An imaging stand in the related art has a structure in which a detector and a grid are mounted on the same plate. In order to perform X-ray imaging of the subject, a center of the detector and a center of the grid need to match. Accordingly, in the related art, when a shape and a size of the detector did not match a shape and a size of the grid, it was difficult to fix the detector and the grid together by the same imaging stand, and thereby X-ray imaging could not be performed.

However, in the imaging stand 50 according to the embodiment of the present disclosure, even when shapes and sizes of the detector 31 and the grid 32 are different, both the detector 31 and the grid 32 are fixed by the single imaging stand 50, and X-ray imaging may be performed smoothly. In the imaging stand 50 according to the embodiment of the present disclosure, there is a wide choice of selection of products of the detector 31 and the grid 32.

Figure 7:
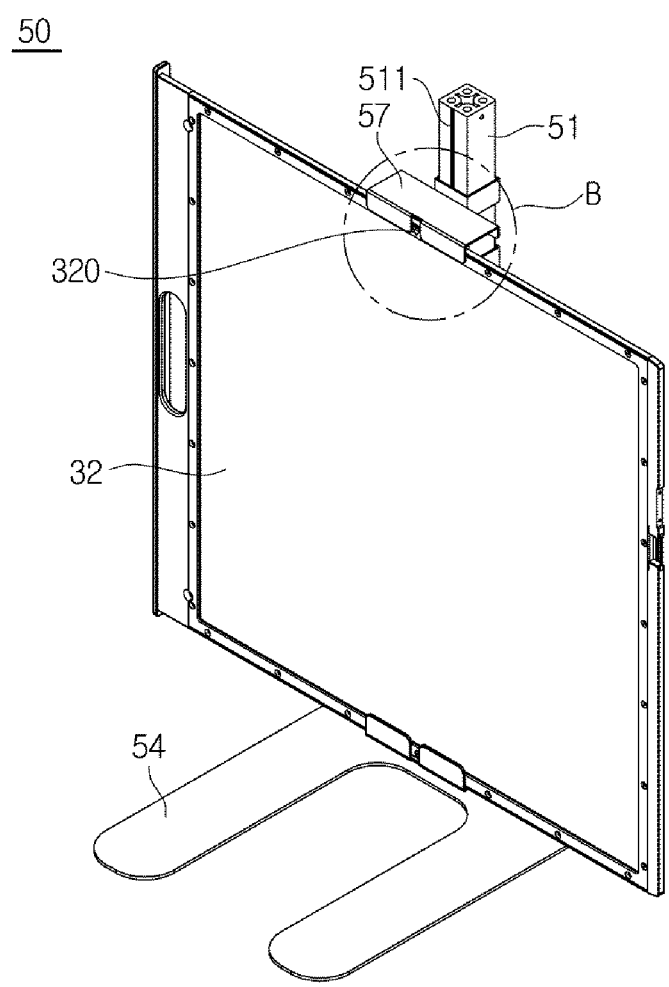
FIG. 7 is a diagram illustrating an appearance in which a grid is located in the imaging stand according to the embodiment of the present disclosure.
Figure 8:
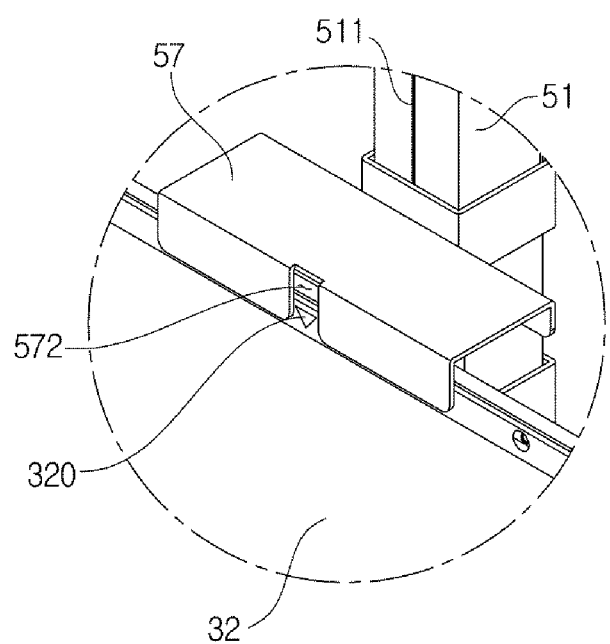
FIG. 8 is a partial perspective view illustrating a part B in FIG. 7.

FIG. 7 is a diagram illustrating an appearance in which the grid is provided in the imaging stand according to the embodiment of the present disclosure. FIG. 8 is a partial perspective view illustrating a part B in FIG. 7.

As illustrated in FIGS. 7 and 8, in the imaging stand 50 according to the embodiment of the present disclosure, a center line 511 may be provided to match centers of the detector 31 and the grid 32. The center line 511 may be provided in the frame 51. The center line 511 may be provided in the vertical direction, which is the length direction of the frame 51. The center line 511 may be a line displayed in the outer circumferential surface of the frame 51, or may also be provided in the form of a groove.

When the operator places the detector 31 on the first plate 52, it is possible to match a center mark displayed in the detector 31 and a location of the center line 511 provided in the frame 51. When the grid 32 is placed in front of the detector 31, the operator may match a center mark 320 displayed in the grid 32 and the center line 511 provided in the frame 51. Therefore, centers of the detector 31 and the grid 32 may be matched.

In the first fixing unit 561 or the third fixing unit 571, a predetermined part is cut and formed such that the center mark provided in the detector 31 or the grid 32 is exposed. For example, as illustrated in FIG. 8, in the third fixing unit 571, a cutting part 572 may be formed by cutting a part such that the center mark 320 displayed in the grid 32 is exposed.

By providing the center line 511 as described above, even when the grid 32 having a shape different from the detector 31 is used to perform X-ray imaging, it is easy to match the centers of the detector 31 and the grid 32.

Centers of the detector 31 and the grid 32 in the vertical direction may be matched using the center line 511 as described above. Centers of the detector 31 and the grid 32 in the horizontal direction may be easily matched such that the grid 32 is arranged in the second fixing holder 530 to expose the center mark displayed in a left or right side of the detector 31 and then a height of the second plate 53 is adjusted.

The detector 31 and the grid 32 having various sizes and shapes may be mounted on the imaging stand 50 according to the embodiment of the present disclosure. While the fixing device 55 is pressed, the first plate 52 or the second plate 53 may move in the vertical direction. Since the first plate 52 or the second plate 53 may be fixed in the frame 51 only when the external force applied to the fixing device 55 is released, it is easy to adjust a height of the detector 31 or the grid 32.

According to the embodiment of the present disclosure, it is possible to easily place the detector and the grid at a desired height of the imaging stand. Also, it is possible to fix the detector and the grid having various sizes and shapes in a single imaging stand.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. An imaging stand, comprising:
    a frame;
    a plate provided to be movable along the frame and having a first plate and a second plate; and
    a fixing device provided on a rear surface of the plate and configured to have elastic force pressing the frame when fixed in the frame, the fixing device having a first fixing device provided on a rear surface of the first plate and a second fixing device provided on a rear surface of the second plate,
    wherein the first fixing device comprises a connecting part mounted on the rear surface of the first plate and an opening facing the connecting part of the first fixing device, and
    the second fixing device comprises a connecting part mounted on the rear surface of the second plate and an opening facing the connecting part of the second fixing device,
    the first fixing device and the second fixing device are disposed parallel with each other also that the opening of the first fixing device and the opening of the second fixing device face toward the same direction.

2. The imaging stand according to claim 1, wherein the fixing device is configured so that, when force opposite to the elastic force is applied to the fixing device, the fixing device is movable in a length direction of the frame.

3. The imaging stand according to claim 1, wherein the fixing device includes:
    a first pressing part in which a first hole through which the frame penetrates is formed; and
    a second pressing part that faces the first pressing part, the second pressing part being formed such that a minimum distance to the first pressing part becomes longer from one side to the other side, and in which a second hole through which the frame penetrates is formed.

4. The imaging stand according to claim 3, wherein the fixing device is configured so that when external force is applied such that a distance between the other side of the first pressing part and the other side of the second pressing part becomes shorter, a fixing state of the fixing device is released and the plate is movable along the frame.

5. The imaging stand according to claim 4, wherein the fixing device is configured so that when the external force applied to the other side of the first pressing part and the other side of the second pressing part is released, an inner side surface of the fixing device forming the first hole or the second hole presses the frame, thereby fixing the fixing device in the frame.

6. The imaging stand according to claim 1, wherein a plurality of fixing grooves into which an inner side surface of the fixing device forming a first hole or a second hole is inserted are formed in an outer surface of the frame.

7. The imaging stand according to claim 6, wherein the plurality of fixing grooves extend in a direction orthogonal to an extending direction of the frame.

8. The imaging stand according to claim 1, wherein a fixing holder configured to support an X-ray detecting unit is provided on a lower end of the plate, and a moving holder configured to fix an upper side of the X-ray detecting unit and be movable along the frame is provided on an upper side of the plate.

9. The imaging stand according to claim 8, wherein the moving holder moves along the frame due to the force of gravity.

10. The imaging stand according to claim 1, wherein the first plate is provided with a detector therein and the second plate is provided with a grid therein.

11. The imaging stand according to claim 10, wherein a first fixing holder configured to support the detector is provided on a lower end of the first plate, and a first moving holder configured to fix an upper side of the detector and be movable along the frame is provided on an upper side of the first plate.

12. The imaging stand according to claim 10, wherein a second fixing holder configured to support the grid is provided on a lower end of the second plate, and a second moving holder configured to fix an upper side of the grid and be movable along the frame is provided on an upper side of the second plate.

13. The imaging stand according to claim 10, wherein either the first plate or the second plate is formed by cutting a part of the other plate.

14. The imaging stand according to claim 1, wherein a center line extending in a length direction of the frame is provided on the frame.

* * * * *